United States Patent [19]

Friedman

[11] Patent Number: 4,492,700

[45] Date of Patent: Jan. 8, 1985

[54] 3-HALO-2-THIOPYRAZINES AS ANTIMICROBIAL AGENTS

[75] Inventor: Arthur J. Friedman, Marlboro, N.J.

[73] Assignee: Merck & Co., Inc., Rahway, N.J.

[21] Appl. No.: 544,949

[22] Filed: Oct. 24, 1983

[51] Int. Cl.³ .................. C07D 241/16; A61K 31/495
[52] U.S. Cl. ...................................... 424/250; 544/357; 544/408
[58] Field of Search ................. 544/357, 408; 424/250

[56] References Cited

U.S. PATENT DOCUMENTS

| | | | |
|---|---|---|---|
| 3,089,809 | 5/1963 | Kinugawa et al. | 424/250 |
| 4,101,546 | 7/1978 | Mixan et al. | 544/406 |
| 4,113,724 | 9/1978 | Portnoy | 544/408 |

FOREIGN PATENT DOCUMENTS

| | | | |
|---|---|---|---|
| 164607 | 6/1979 | Japan | 43/60 |
| 167206 | 12/1980 | Japan | 424/250 |
| 164606 | 12/1980 | Japan | 424/250 |

*Primary Examiner*—Robert Gerstl
*Assistant Examiner*—William A. Teoli, Jr.
*Attorney, Agent, or Firm*—Alice O. Robertson; R. Brent Olson

[57] ABSTRACT

The instant invention is directed to a compound represented by the formula:

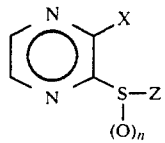

wherein:

X is a chloro or bromo radical;

Z is a chloro, bromo, amino, amino mono- and di-substituted by lower alkyl, 3-halo-pyrazinyl-2-thio, cyano, $$-C(S)-NR_3R_4,$$

wherein $R_3$ and $R_4$ independently are methyl or ethyl, benzylidineamino, lower alkyl substituted benzylidineamino group; and n is 0 or 1, provided that when n is 1, Z is a benzylidineamino or lower alkyl substituted benzylidineamino group.

9 Claims, No Drawings

3-HALO-2-THIOPYRAZINES AS ANTIMICROBIAL AGENTS

DESCRIPTION OF THE INVENTION

The present invention is directed to certain sulfur-containing pyrazine compounds represented by the Formula I:

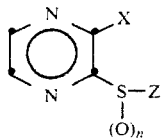
I

In this and succeeding formulas, X is halo; Z is a halo, an amino, a halopyrazinylthio, a cyano, a dithiocarbamyl or an arylideneamino group, and n is 0 or 1, provided that when n is 1, Z is an arylmethylideneamino group.

By "halo" is meant chloro or bromo.

By "amino" is meant unsubstituted amino or amino substituted with lower alkyl radicals generally from 1 to 4 carbon atoms. It is inclusive of disubstituted amino and may be represented by $-NR_1R_2$ wherein $R_1$ and $R_2$ independently may be H or lower alkyl.

By "halopyrazinylthio" is meant 3-halopyrazinyl-2-thio.

By "dithiocarbamyl" is meant substituted dithiocarbamyl groups and may be represented by

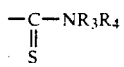

wherein $R_3$ and $R_4$ independently are methyl or ethyl.

By "arylmethylideneamino" is meant benzylideneamino or substituted benzylideneamino wherein the substituent is a lower alkyl group and which may be represented by

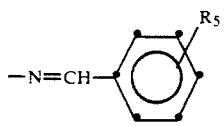

wherein $R_5$ is H or lower alkyl.

The products of this invention are generally light-amber or yellow colored solids or moderate melting point and soluble in many organic solvents such as tetrahydrofuran, diethyl ether, carbon tetrachloride, diisopropyl ether, chloroform, methylene chloride, and the like.

The compounds of the present invention are useful as antimicrobial agents, especially for the control of yeast and fungi. Thus, they have been demonstrated to be useful especially against Saccharomyces yeast genus, and against various fungi genera such as Aspergillus, Pullularia, Penicillium, and Alternaria. Certain of the compounds in addition to having antimicrobial properties are useful as intermediates for the synthesis of other sulfur compounds.

The method of preparation of the sulfur compounds of present invention depends on the particular compound.

Compounds represented by Formula II:

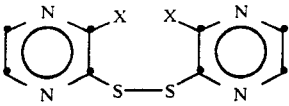
II may be obtained from 2,3-dihalopyrazine by reacting said compound with sodium hydrosulfide hydrate to obtain 3-halopyrazinethiol sodium salt dihydrate intermediate which may thereafter be reacted in the presence of potassium iodide and iodine to obtain the desired 2,2'-dihalo-dithiobis-3-pyrazine product.

In carrying out the reaction, first the 2,3-dihalopyrazine is stirred together with about a fourfold molar excess of sodium hydrosulfide hydrate in a polar solvent such as ethanol or isopropanol and heated with continued stirring initially at reflux temperature for about 1 hour and thereafter at ambient temperature for several hours or conveniently overnight. As a result of these operations, a reaction takes place with the formation of the 3-halopyrazinethiol sodium salt dihydrate intermediate which separates in the reaction mixture. The sodium salt is then recovered, purified, if desired, then reacted with potassium iodide and iodine by adding an aqueous solution thereof to an aqueous solution of the sodium salt intermediate and stirring. Usually a reaction takes place substantially immediately with the formation of 2,2'-dihalodithiobis-3-pyrazine product which separates in the reaction mixture. The product may be recovered by filtration and purified employing conventional methods.

The 2,2'-dihalodithiobis-3-pyrazine may be employed for the preparation of 3-halo-2-pyrazine-sulfenamide compounds represented by Formula III:

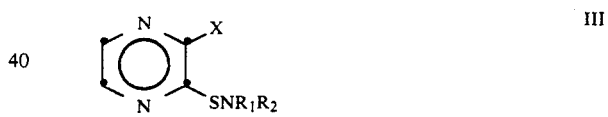
III

The 3-halo-2-pyrazinesulfenamide compounds may be prepared by reacting 2,2'-dihalo-dithiobis-3-pyrazine first with silver nitrate then with ammonia or amine, represented by $R_1R_2NH$.

The reaction may be carried out by adding with stirring the 2,2'-dihalodithiobis-3-pyrazine to a solution of silver nitrate in a polar solvent, thereafter cooling the reaction mixture to about 0° to 5° C. and adding $R_1R_2NH$ thereto. If $R_1R_2NH$ is ammonia, ammonia gas is passed into the mixture until the mixture is saturated with ammonia; if it is an amine, an appropriate amount of the amine is added portionwise to the mixture. The mixture is then cooled and stirred for several hours, conveniently overnight to obtain the desired 3-halo-2-pyrazinesulfenamide product and 3-halopyrazinethiol silver salt as by-product. After completion of the reaction, the reaction mixture is filtered to remove and recover the white solid silver salt by-product and the filtrate is evaporated to dryness to obtain the product as a solid residue. The residue is extracted with an inert solvent such as diethyl ether. The solvent ether is vaporized from the extract to obtain a purified residue which is recrystallized from ethyl alcohol to obtain the desired 3-halo-2-pyrazinesulfenamide product as a white crystalline solid.

Substantially equimolar amounts of the reactants are employed. The reaction may be carried out in the number of polar solvents, however, solvents such as methanol or other alkanols are preferred. If the sulfenamide is an N-substituted sulfenamide, the reactant is an amine.

When the sulfur compound is a 3-halo-2-pyrazinesulfenyl halide, it may be represented by Formula IV and wherein Y is halogen, i.e., chlorine or bromine.

 IV

The 3-halo-2-pyrazinesulfenyl halide compounds may be prepared by reacting 2,2'-dihalodithiobis-3-pyrazine with chlorine or bromine in the presence of a catalytic amount of iodine. When the solid halo product is a sulfenyl chloride compound, the reaction is carried out by bubbling chlorine gas through the reaction mixture containing a catalytic amount of iodine while the mixture is being warmed. When the compound is to be a sulfenyl bromide compound, liquid bromine is added dropwise to the liquid mixture containing catalyst. After completion of the addition of chlorine or bromine, the reaction mixture is stirred from several minutes to several hours. At the end of this period, the reaction mixture is purged with nitrogen and the desired sulfenyl halide product recovered as residue. The product may be recrystallized if desired from aprotic solvents such as carbon tetrachloride.

When the sulfur compound is a 2-halo-3-thiocyanatopyrazine product, it may be represented by Formula V:

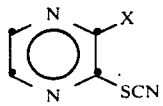 V

The 2-halo-3-thiocyanatopyrazine may be prepared by the reaction of trimethylsilyl cyanide with 3-halo-2-pyrazinesulfenyl halide in an atmosphere of nitrogen. The reaction may be carried out by dissolving the 3-halo-2-pyrazinesulfenyl halide in a solvent such as acetonitrile and adding thereto while cooling under an atmosphere of nitrogen a molar equivalent of trimethylsilyl cyanide. After completion of the addition, the reaction mixture is stirred at ambient temperature, conveniently overnight. At the end of this period, the solvent and the unreacted trimethylsilyl cyanide are removed by passing a stream of nitrogen over the reaction mixture to carry away the cyanide and solvent, and the desired 2-halo-3-thiocyanatopyrazine product is recovered as residue. The product may be recrystallized, if desired, from ethanol or other alcohol solvent.

When the product is N-arylmethylidene-2-halopyrazine-3-sulfenamide, it may be represented by Formula IV:

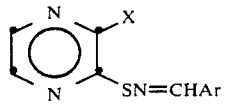 VI

N-arylmethylidene-2-halopyrazinesulfenamide may be prepared by reacting substantially equimolar portions of 3-halo-2-pyrazinesulfenamide, the appropriate aromatic aldehyde and ammonium chloride.

In carrying out the reaction, the reactants are mixed together in an alcoholic solvent and heated together at reflux temperature to cause a reaction to take place with the formation of the desired N-arylmethylidine-2-halopyrazine-3-sulfenamide product in the reaction mixture. The product is recovered as residue by vaporizing the solvent, preferably at reduced pressure, and may be crystallized from a hot solvent such as chloroform or methylene chloride.

When the product is a 2-halo-3-dithiocarbamylpyrazine, it may be represented by the Formula VII:

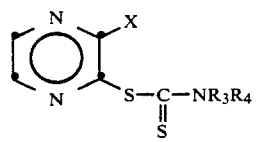 VII

2-Halo-3-dithiocarbamylpyrazine may be prepared by reacting 3-halopyrazinethiol sodium salt with an appropriate thiocarbamyl chloride represented by the formula

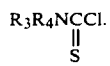

Preferred 2-halo-3-dithiocarbamylpyrazine compounds are N,N-dialkylated compounds especially N,N-diethyl and N,N-dimethyl compounds.

In carrying out the reaction, the reactants are mixed together in an inert solvent such as tetrahydrofuran and the mixture stirred generally with heating at reflux temperature for from 1 to 2 hours, and then allowed to continue stirring and reacting at ambient temperature, conveniently overnight. At the end of the period the mixture is filtered and the solvent vaporized to obtain as residue a 2-halo-3-dithiocarbamylpyrazine product. The product is recrystallized, generally first from a non-polar solvent such as chloroform or methylene chloride and thereafter from a polar solvent such as ethanol and other alcohol.

When the product is N-arylmethylidine-2-halopyrazine-3-sulfinamide, it may be represented by formula VIII:

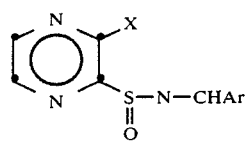 VIII

N-arylmethylidene-2-halopyrazine-3-sulfinamide may be prepared by reacting N-arylmethylidine-2-halopyrazine-3-sulfenamide with an oxidizing agent such as peracid or peroxide in a mildly alkaline solution for time sufficient to form the desired sulfinamide product.

In carrying out the reaction, a solution of N-arylmethylidene-2-halopyrazine-3-sulfenamide in a non-polar solvent such as chloroform is added to a rapidly stirring aqueous solution of sodium bicarbonate or similar mild base and the resulting mixture cooled to a temperature in the range of −5° to +5° C. To the cooled solution then is added dropwise with stirring, a solution of a peracid in an inert organic solvent. After completion of the addition, stirring is continued for several hours, preferably overnight, to obtain a N-arylmethylidene-2-halopyrazine-3-sulfinamide product which remains dissolved in the organic solvent. The organic solution is separated, dried, and the solvent then vaporized to obtain the desired product as residue. The product may be purified by recrystallization.

The following examples illustrate the invention but are not to be construed as limiting:

EXAMPLE I 2,2'-Dichlorodithiobis-3-pyrazine

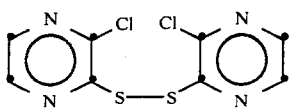

Preparation of 3-chloropyrazinethiol sodium salt dihydrate starting material. 3.73 grams (0.025 mole) of 2,3-dichloropyrazine, 5.61 grams (0.10 mole) of sodium hydrosulfide hydrate and 100 milliliters of ethanol were heated at reflux temperature for one hour and thereafter stirred at ambient temperature overnight whereupon a reaction took place with the formation of a solid product. The product after recrystallization twice from ethanol had the following elemental analyses.

Calcd. for $C_4H_6ClN_2NaO_2S$ (m.w. 204.61), C, 23.48; H, 2.96; N, 13.69; Na, 11.24; Cl, 17.32; S, 15.67. Found: C, 23.42; H, 2.90; N, 13.66; Na, 11.18; Cl, 17.05; S, 15.60.

Preparation of 2,2'-dichlorodithiobis-3-pyrazine. A solution of 0.32 gram (0.004 mole) of potassium iodide and 0.25 gram (0.001 mole) of iodine in 50 milliliters of water was added dropwise to a stirred solution of 0.41 gram (0.002 mole) of 3-chloropyrazinethiol sodium salt dihydrate in 25 milliliters of water over a period about 10 minutes. After completion of the addition, stirring was continued for additional 10 minutes to complete the formation of 2,2'-dichlorodithiobis-3-pyrazine product which precipitated in the reaction mixture. The precipitate was recovered by filtration, washed with water and dried to obtain a purified product of melting point 165°–166° C. in a quantitative yield. Elemental analyses for the product were as follows:

Calcd. for $C_8H_4Cl_2N_4S_2$ (m.w. 291.18), C, 33.00; H, 1.38; Cl, 24.35; S, 22.02. Found: C, 32.85; H, 1.30; Cl, 24.54; S, 21.53.

EXAMPLE II

In a similar operation, 2,2'-dibromodithiobis-3-pyrazine may be prepared by reacting 2,3-dibromopyrazine with excess sodium hydrosulfide hydrate to obtain 3-bromo-pyrazinethiol sodium salt and thereafter reacting the latter with an aqueous mixture of potassium iodide and iodine.

EXAMPLE III

3-Chloropyrazinesulfenamide

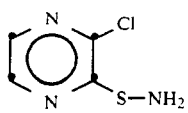

To a solution of 0.89 gram (0.005 mole) of silver nitrate in 50 milliliters of methanol was added while stirring 1.45 grams (0.005 mole) of 2,2'-dichlorodithiobis-3-pyrazine. The reaction mixture was cooled to 0° C. and a stream of ammonia gas passed into the reaction mixture for about fifteen minutes, after which time stirring was continued for about 18 hours to obtain a solid therein. The reaction mixture was filtered to remove and recover a white solid and the filtrate evaporated to dryness to obtain a solid residue. The solid residue was extracted with diethyl ether and the ether vaporized from ether extract to obtain a purified residue. The latter was recrystallized from ethyl alcohol to obtain 0.2 gram of white crystalline 3-chloro-2-pyrazinesulfenamide product, m.p. 113°–114° C. Elemental analyses were as follows:

Calcd. for $C_4H_4ClN_3S$ (m.w. 161.61) C, 29.73; H, 26.00; Cl, 21.44; N, 2.49; S, 19.84. Found: C, 29.68; H, 25.98; Cl, 21.86; N, 2.46; S, 20.10.

EXAMPLE IV

In similar operations except that the amine is added dropwise to the reaction mixture, the following compounds may be prepared:

N,N-dimethyl-3-chloro-2-pyrazine-sulfenamide from 2,2'-dichlorodithiobis-3-pyrazine and dimethylamine.

N-(n-Propyl)-3-chloro-2-pyrazinesulfenamide from 2,2'-dichlorodithiobis-3-pyrazine and n-propylamine.

N-Ethyl-3-bromo-2-pyrazinesulfenamide from 2,2'-dibromodithiobis-3-pyrazine and ethylamine.

N-Methyl-3-bromo-2-pyrazinessulfenamide from 2,2-dibromodithiobis-3-pyrazine and methylamine.

N-Ethyl, N-methyl-3-chloro-2-pyrazine-sulfenamide from 2,2'-dichlorodithiobis-3-pyrazine and methyl ethylamine.

EXAMPLE V

3-Chloro-2-pyrazinesulfenyl chloride

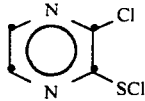

A solution of 1.90 grams (0.0065 mole) of 2,2'-dichlorodithiobis-3-pyrazine in 50 milliliters of carbon tetrachloride was stirred and heated to 55±5° C. and while being heated, a catalytic amount of iodine was added and chlorine bubbled through the solution for about fifteen minutes. At the end of this period, the reaction mixture was purged with nitrogen and the solvent removed in vacuo to produce 2.35 grams (quantitative yield) of the desired sulfenyl chloride product.

EXAMPLE VI

In operation similar to that described in Example V, the following compounds may be prepared:

3-Chloro-2-pyrazinesulfenyl bromide by the dropwise addition of bromine to a solution of 2,2'-dichlorodithiobis-3-pyrazine in carbon tetrachloride in the presence of a catalytic amount of iodine.

3-Bromo-2-pyrazinesulfenyl bromide by similar addition of bromine to a solution of 2,2'-dibromodithiobis-3-pyrazine in carbon tetrachloride in the presence of a catalytic amount of iodine.

3-Bromo-2-pyrazinesulfenyl chloride by bubbling chlorine through a solution of 2,2'-dibromodithiobis-3-pyrazine in carbon tetrachloride in the presence of a catalytic amount of iodine.

EXAMPLE VII

2-Chloro-3-thiocyanatopyrazine

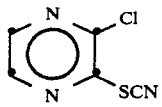

1.81 grams (0.01 mole) of 3-chloro-2-pyrazinesulfenyl chloride was dissolved in acetonitrile with stirring under nitrogen at 0° C. To the stirred solution, 0.99 gram (0.01 mole) of trimethylsilyl cyanide was added rapidly and the stirring continued for 18 hours. At the end of this period, the acetonitrile and residual trimethylsilyl cyanide were removed by blowing a stream of nitrogen over the reaction mixture and the desired product recovered as residue. The product was crystallized from ethanol to obtain a purified product, m.p. 70°–71° C., in an amount of 0.64 gram. The product had elemental analyses as follows:

Calcd. for $C_5H_2ClN_3S$ (m.w. 171.61). C, 35.00; H, 1.17; Cl, 20.66; N, 24.49; S, 18.68. Found: C, 34.67; H, 1.19; Cl, 20.68; N, 23.44; C, 34.72; H, 1.22; N, 23.44; S, 18.82.

EXAMPLE VIII

In a similar manner, 2-bromo-3-thiocyanatopyrazine is prepared from 3-bromo-2-pyrazinesulfenyl chloride and trimethylsilyl cyanide.

EXAMPLE IX

N-Benzylidene-2-chloropyrazine-3-sulfenamide

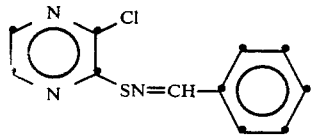

0.65 gram (3.2 millimoles) of 3-chloro-2-pyrazinesulfenamide, 0.34 gram (3.2 millimoles) of benzaldehyde and 0.16 gram (3.2 millimoles) of ammonium chloride in 80 milliliters of ethanol were heated together with stirring at reflux temperature whereupon a reaction took place with the formation of an N-benzylidene-2-chloropyrazine-3-sulfenamide product in the reaction mixture. The product was recovered as residue by vaporizing the solvent and was crystallized from hot chloroform to obtain a purified product, m.p. 93°–94° C. Elemental analyses of the product were as follows:

Calcd. for $C_{11}H_8ClN_3S$ (m.w. 249.72). C, 52.91; H, 3.23; N, 16.83. Found: C, 52.72; H, 3.12; N, 16.85.

EXAMPLE X

In a manner similar to that described in Example IX, the following compounds are prepared:

N-(p-Tolyl)methylidene-2-chloropyrazine-3-sulfenamide from 3-chloro-2-pyrazinesulfenamide, tolualdehyde and ammonium chloride.

N-(4-Isopropylbenzylidene)-2-chloropyrazine-3-sulfenamide from 3-chloro-2-pyrazinesulfenamide, 4-isopropylbenzaldehyde and ammonium chloride.

N-(3,4-Dimethylbenzylidene)-2-chloropyrazine-3-sulfenamide from 3-chloro-2-pyrazinesulfenamide, 3,4-dimethylbenzaldehyde and ammonium chloride.

N-(o-Tolyl)methylidene-2-bromopyrazine-3-sulfenamide from 3-bromo-2-pyrazinesulfenamide, o-tolualdehyde and ammonium chloride.

N-Benzylidene-2-bromopyrazine-3-sulfenamide from 3-bromo-2-pyrazinesulfenamide, benzaldehyde and ammonium chloride.

EXAMPLE XI

2-Chloro-3-(N,N-dimethyldithiocarbamyl)pyrazine

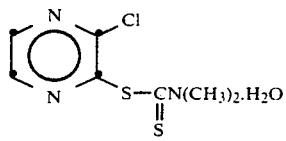

2.05 grams (0.01 mole) of 3-chloropyrazinethiol sodium salt dihydrate and 1.27 grams (0.01 mole) of N,N-dimethylthiocarbamyl chloride were mixed together in 50 milliliters of tetrahydrofuran and the mixture stirred with heating at reflux temperature for 1 hour and at ambient temperature for 18 hours. At the end of this period the mixture was filtered and the solvent vaporized to obtain as residue an orange oil which solidified to a crystalline mass on standing. The solid was recrystallized from a chloroform and then from ethanol to obtain a 2-chloro-3-(N,N-dimethyldithiocarbamyl)-pyrazine product in a yield of 1.67 grams (71 percent). The product was recrystallized from ethanol. The product calculated for hydrate gave the following elemental analyses:

Calcd. for $C_7H_{10}ClN_3S_2$ (m.w. 251.76). C, 33,40; H, 4.00; Cl, 14.08; N, 16.69; S, 25.47. Found: C, 33.94; H, 3.55; Cl, 14.24 (15.10); N, 16.96; S, 24.00 (25.47).

EXAMPLE XII

In similar operations, the following compounds may be prepared:

2-Chloro-3-(N,N-diethyldithiocarbamyl)pyrazine from 3-chloropyrazinethiol sodium salt dihydrate and N,N-diethylthiocarbamyl chloride.

2-Bromo-3-(N,N-diethyldithiocarbamyl)pyrazine from -3-bromopyrazinethiol sodium salt dihydrate and N,N-diethyldithiocarbamyl chloride.

2-Chloro-3-(N,N-dimethyldithiocarbamyl)pyrazine from 3-chloropyrazinethiol sodium salt dihydrate and N,N-dimethyldithiocarbamyl chloride.

2-Bromo-3-(N,N-dimethyldithiocarbamyl)pyrazine from 3-bromopyrazinethiol sodium salt dihydrate and N,N-dimethyldithiocarbamyl chloride.

EXAMPLE XIII

| Compound | MINIMUM INHIBITORY CONCENTRATION (ppm) | | | | |
|---|---|---|---|---|---|
| | Saccharomyces cerevisiae | Aspergillus niger | Pullularia pullulans | Penicillium funiculosum | Alternaria brassicicola |
| N—Benzylidene-2-chloropyrazine-3-sulfenamide | 50 | 200/400 | 50 | 100/200 | 50 |
| 2-Chloro-3-thiocyanatopyrazine | 50 | 50 | 10 | 10 | 10 |
| 2-Chloropyrazine-3-sulfenamide | 1000 | 1000 | 50 | 50 | 50 |
| 2,2'-Dichlorodithiobis-3-pyrazine | 1000 | 1000 | 50 | 1000 | 100 |
| 2-Chloro-3-(N,N—dimethyl)-dithiocarbamyl)pyrazine | 200 | 50 | 10/50 | 100 | 50 |

N-Benzylidene-2-chloropyrazine-3-sulfinamide

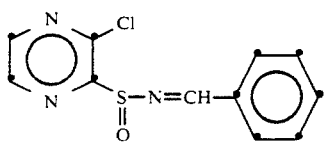

1.25 grams (0.005 mole) of N-benzylidene-2-chloropyrazine-3-sulfenamide in 25 milliliters of chloroform was added to a rapidly stirring mixture of 0.69 gram (0.25 millimole) of sodium bicarbonate and the resulting mixture cooled to 0° C. To the cooled solution, a solution of gram (5.5 millimole) of m-chloroperbenzoic acid in 25 milliliter of chloroform was added dropwise over a 15 minute period. After completion of the addition, stirring was continued for 15 hours. At the end of this period, chloroform layer was separated from the aqueous layer, dried over anhydrous potassium carbonate, and subjected to reduced pressure to remove the solvent and to recover as residue an oil which solidified on standing. The latter was purified by crystallization from ethanol to obtain the desired N-benzylidene-2-chloropyrazine-3-sulfinamide product, m.p. 113°–114° C. Elemental analyses were as follows:

Calcd. for $C_{11}H_8ClN_3O_5$ (m.w. 265.72). C, 49.72; H, 3.03; N, 15.81. Found: C, 49.79; H, 3.11; N, 15.64.

EXAMPLE XIV

In similar preparations, the following compounds may be prepared:

N-Benzylidene-2-bromopyrazine-3-sulfinamide from N-benzylidene-2-bromopyrazine-3-sulfenamide and m-chloroperbenzoic acid.

N-(p-Tolyl)methylidene-2-chloropyrazine-3-sulfinamide from N-(p-tolyl)methylidene-2-chloropyrazine sulfenamide and m-chloroperbenzoic acid.

The properties useful for controlling yeast and fungi were discovered in a test which is carried out in the following manner:

A stock solution of a compound to be tested for antimicrobial activity is prepared in 25% methanol. Dilutions of the stock solution are made into Sabouraud maltose agar, and the agar poured into sterile petri dishes. After hardening, the plates are streaked with an aqueous suspension of the test organism. The inoculated plates are incubated at about 30° C. and the readings made after 4 to 5 days' incubation to determine fungal growth. The lowest concentration that inhibits fungal growth is recorded as minimum inhibitory concentration. The results showing antifungal activity may be seen in the following table:

Although the compounds are most effective against fungal organisms, they are also useful against yeast as seen above and also against bacteria. Especially outstanding against bacteria were 2-chloro-3-thiocyanatopyrazine which exhibited controls at concentration against Aerobacter aerogenes at minimum inhibitory concentrations of 50 and 100 ppm, and against Pseudomonas aeruginosa of 200 ppm, and 2-chloro-3-(N,N-dimethyldithiocarbamyl)pyrazine which exhibited controls against the same organisms at minimum inhibitory concentrations of 400 ppm and 200 ppm, respectively.

In employing the sulfur-containing pyrazine compounds of the present invention for antimicrobial control, compositions containing said sulfur pyrazine compounds may be prepared in a liquid, solid or aerosol inert carrier to be applied to the substrate or area where antimicrobial control is desired. Such compositions may contain the sulfur-containing pyrazine compounds in an amount of from about 0.1 percent to 10 percent by weight, or if concentrate composition, up to 95 percent by weight. Inert carriers include liquids such as petroleum distillates, kerosene, aromatic hydrocarbons and the like, and finely divided solids such as surface active agents, clays, diatomaceous earth, bentonite, mahogany soaps, talc, attapulgite and the like. Solid carriers which have surface active properties are useful also for preparing emulsion and dispersions. The compositions may be diluted or employed without modification to provide an antimicrobially effective amount of the sulfur pyrazine compound in the substrate or area to be controlled of at least about 50 parts per million by weight and up to 10,000 parts per million or more, depending on the organism and substrate.

3-Halopyrazinethiol sodium salt obtained as a dihydrate is a novel compound which is an intermediate in the preparation of 2,2'-dihalodithiobis-3-pyrazine product (Formula II) and may be obtained by the reaction of 2,3-dihalopyrazine and sodium hydrosulfide hydrate as described in connection with the preparation of 2,2'-dihalodithiobis-3-pyrazine. It is also an intermediate in the preparation of 2-halo-3-(N,N-dialkyldithiocarbamyl)pyrazine (Formula VII). In addition to being useful as an intermediate, it also has certain antimicrobial properties. Thus 3-chloropyrazinethiol soduim salt, dihydrate had a minimum inhibitory concentration against Saccharomyces cerevisiae, Pullularia pullulans, Penecillium funiculosum and Alternaria brassicicola of 50 ppm.

The starting materials generally are available commercially or their preparation described in the literature.

The starting material 2,3-dibromopyrazine may be prepared from 2,3-dichloropyrazine by heating it with phosphorus tribromide. In a representative preparation 10 grams of 2,3-dichloropyrazine and 30 milliliters of phosphorus tribromide were stirred and heated at reflux temperature for 24 hours to obtain 2,3-dibromopyrazine in the reaction mixture. It was recovered from the mixture by cooling to ambient temperature and pouring over crushed ice whereupon a white solid separated. The latter was recovered, dried and crystallized from ethanol to obtain white acicular crystals of melting point 45°–46° C.

What is claimed is:

1. A compound represented by the formula:

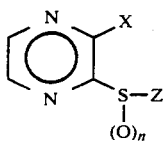

wherein:

X is a chloro or bromo radical;

Z is a chloro, bromo, amino, amino mono- and di-substituted by lower alkyl, 3-halo-pyrazinyl-2-thio, cyano,

—C(S)—NR$_3$R$_4$, wherein R$_3$ and R$_4$ independently are methyl or ethyl, benzylidineamino, lower alkyl substituted benzylidineamino group; and n is 0 or 1, provided that when n is 1, Z is a benzylidineamino or lower alkyl substituted benzylidineamino group.

2. A compound according to claim 1 in which Z is a chloro or bromo group.

3. A compound according to claim 1 in which Z is an amino group.

4. A compound according to claim 1 in which Z is a cyano group.

5. A compound according to claim 1 in which Z is a benzylidineamino or lower alkyl substituted benzylidineamino group.

6. A compound according to claim 1 in which Z is 3-halo-pyrazinyl-2-thio.

7. A compound according to claim 1 in which Z is

—C(S)—NR$_3$R$_4$ wherein

R$_3$ and R$_4$ independently are methyl or ethyl.

8. An antimicrobial composition comprising an inert carrier and an antimicrobially effective amount of a compound of claim 1.

9. A method for inhibiting microbial growth which comprises applying an antimicrobially effective amount of a compound of claim 1.

* * * * *